(12) United States Patent
Quick

(10) Patent No.: US 8,758,214 B2
(45) Date of Patent: *Jun. 24, 2014

(54) RADIATION CATHETER WITH MULTILAYERED BALLOON

(71) Applicant: Hologic, Inc., Bedford, MA (US)

(72) Inventor: Richard L. Quick, Mission Viejo, CA (US)

(73) Assignee: Hologic, Inc., Bedford, MA (US)

( * ) Notice: Subject to any disclaimer, the term of this patent is extended or adjusted under 35 U.S.C. 154(b) by 96 days.

This patent is subject to a terminal disclaimer.

(21) Appl. No.: 13/649,668

(22) Filed: Oct. 11, 2012

(65) Prior Publication Data

US 2013/0079580 A1    Mar. 28, 2013

Related U.S. Application Data

(63) Continuation of application No. 11/716,758, filed on Mar. 12, 2007, now Pat. No. 8,287,442.

(51) Int. Cl.
*A61N 5/00* (2006.01)
*A61N 5/10* (2006.01)

(52) U.S. Cl.
CPC ............ *A61N 5/1007* (2013.01); *A61N 5/1015* (2013.01); *A61N 2005/1003* (2013.01); *A61N 2005/1018* (2013.01)
USPC ............................. 600/3; 600/7; 604/101.02

(58) Field of Classification Search
USPC ........................ 600/1–8; 604/101.01–101.03, 604/103.06–103.12, 508, 509
See application file for complete search history.

(56) References Cited

U.S. PATENT DOCUMENTS

| | | | |
|---|---|---|---|
| 3,324,847 A | 6/1967 | Zoumboulis | |
| 3,872,856 A | 3/1975 | Clayton | |
| 3,975,350 A | 8/1976 | Hudgin et al. | |
| 4,119,094 A | 10/1978 | Micklus et al. | |
| 4,454,106 A | 6/1984 | Gansow et al. | |

(Continued)

FOREIGN PATENT DOCUMENTS

| | | |
|---|---|---|
| EP | 0536440 A1 | 4/1993 |
| EP | 0642766 A2 | 3/1995 |

(Continued)

OTHER PUBLICATIONS

Paul V. Harper, "Some Therapeutic Applications of Radioisotopes", Journal of the Mississippi State Medical Association, Oct. 1966, vol. VII, pp. 526-533.

(Continued)

*Primary Examiner* — Charles A Marmor, II
*Assistant Examiner* — Carrie R Dorna

(57) ABSTRACT

A catheter device for irradiating tissue surrounding a body site within a body of a patient, includes an elongated shaft which has a distal portion configured to be deployed within the body site. A treatment location at the distal portion has one or more radiation guides configured to receive a radiation source to irradiate tissue at least in part surrounding the body site. An inflatable multilayered balloon is located to surround the treatment location with a wall thereof having at least two layers including a first layer separate from, inside, and in contact with a second layer around an entire periphery of the first layer, and each of the first layer and the second layer being secured to the distal portion of the elongated shaft.

20 Claims, 2 Drawing Sheets

(56) References Cited

U.S. PATENT DOCUMENTS

| | | |
|---|---|---|
| 4,571,241 A | 2/1986 | Christopher |
| 4,690,677 A | 9/1987 | Erb |
| 4,763,642 A | 8/1988 | Horowitz |
| 4,929,470 A | 5/1990 | Rittenhouse et al. |
| 4,998,917 A | 3/1991 | Gaiser |
| 4,998,930 A | 3/1991 | Lundahl |
| 5,059,166 A | 10/1991 | Fischell et al. |
| 5,106,360 A | 4/1992 | Ishiwara et al. |
| 5,167,622 A | 12/1992 | Muto |
| 5,199,939 A | 4/1993 | Dake et al. |
| 5,227,969 A | 7/1993 | Waggener et al. |
| 5,259,847 A | 11/1993 | Trambert |
| 5,302,168 A | 4/1994 | Hess |
| 5,312,356 A | 5/1994 | Engelson et al. |
| 5,314,518 A | 5/1994 | Ito et al. |
| 5,336,178 A * | 8/1994 | Kaplan et al. .......... 604/509 |
| 5,342,305 A | 8/1994 | Shonk |
| 5,381,504 A | 1/1995 | Novack et al. |
| 5,411,466 A | 5/1995 | Hess |
| 5,417,687 A | 5/1995 | Nardella et al. |
| 5,428,658 A | 6/1995 | Oettinger et al. |
| 5,429,582 A | 7/1995 | Williams |
| 5,503,613 A | 4/1996 | Weinberger |
| 5,535,817 A | 7/1996 | Dunne |
| 5,566,221 A | 10/1996 | Smith et al. |
| 5,603,991 A | 2/1997 | Kupiecki et al. |
| 5,611,767 A | 3/1997 | Williams |
| 5,616,114 A | 4/1997 | Thorton et al. |
| 5,621,780 A | 4/1997 | Smith et al. |
| 5,624,395 A | 4/1997 | Mikhail et al. |
| 5,653,683 A | 8/1997 | D'Andrea |
| 5,662,580 A | 9/1997 | Bradshaw et al. |
| 5,704,926 A | 1/1998 | Sutton |
| 5,720,717 A | 2/1998 | D'Andrea |
| 5,759,173 A | 6/1998 | Preissman et al. |
| 5,782,742 A | 7/1998 | Crocker et al. |
| 5,820,594 A | 10/1998 | Fontirroche et al. |
| 5,820,717 A | 10/1998 | Siegenthaler |
| 5,863,284 A | 1/1999 | Klein |
| 5,863,285 A | 1/1999 | Coletti |
| 5,899,882 A | 5/1999 | Waksman et al. |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,993,972 A | 11/1999 | Reich et al. |
| 6,022,308 A | 2/2000 | Williams |
| 6,033,357 A | 3/2000 | Ciezki et al. |
| 6,036,631 A | 3/2000 | McGrath et al. |
| 6,083,148 A | 7/2000 | Williams |
| 6,086,970 A | 7/2000 | Ren |
| 6,093,142 A | 7/2000 | Ciamacco, Jr. |
| 6,095,966 A | 8/2000 | Chornenky et al. |
| 6,143,013 A | 11/2000 | Samson et al. |
| 6,200,257 B1 | 3/2001 | Winkler |
| 6,217,565 B1 | 4/2001 | Cohen |
| 6,251,059 B1 | 6/2001 | Apple et al. |
| 6,256,529 B1 | 7/2001 | Holupka et al. |
| 6,282,142 B1 | 8/2001 | Miyawaki |
| 6,306,074 B1 | 10/2001 | Waksman et al. |
| 6,319,188 B1 | 11/2001 | Lovoi |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,413,203 B1 | 7/2002 | Sahatjian |
| 6,413,204 B1 | 7/2002 | Winkler et al. |
| 6,416,492 B1 | 7/2002 | Nielson |
| 6,458,069 B1 | 10/2002 | Tam et al. |
| 6,482,142 B1 | 11/2002 | Winkler et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,605,030 B2 | 8/2003 | Weinberger |
| 6,610,013 B1 | 8/2003 | Fenster et al. |
| 6,615,070 B2 | 9/2003 | Lee |
| 6,673,006 B2 | 1/2004 | Winkler |
| 6,706,014 B2 | 3/2004 | Banik et al. |
| 6,723,052 B2 | 4/2004 | Mills |
| 6,746,392 B2 | 6/2004 | Stiger et al. |
| 6,752,752 B2 | 6/2004 | Geitz |
| 6,770,058 B1 | 8/2004 | Liprie |
| 6,913,600 B2 | 7/2005 | Valley et al. |
| 6,923,754 B2 | 8/2005 | Lubock |
| 6,955,641 B2 | 10/2005 | Lubock |
| 6,983,754 B1 | 1/2006 | Anderson et al. |
| 7,098,463 B2 | 8/2006 | Adamovics |
| 7,107,089 B2 | 9/2006 | Lee |
| 7,171,255 B2 | 1/2007 | Holupka et al. |
| 7,201,715 B2 | 4/2007 | Burdette et al. |
| 7,322,929 B2 | 1/2008 | Lovoi |
| 7,404,791 B2 | 7/2008 | Linares et al. |
| 7,407,476 B2 | 8/2008 | Lubock et al. |
| 7,413,539 B2 | 8/2008 | Lubock et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,662,082 B2 | 2/2010 | White et al. |
| 7,783,006 B2 | 8/2010 | Stewart et al. |
| 7,885,382 B2 | 2/2011 | Stewart et al. |
| 7,887,476 B2 | 2/2011 | Hermann et al. |
| 8,079,946 B2 | 12/2011 | Lubock et al. |
| 2001/0016725 A1 | 8/2001 | Valley et al. |
| 2001/0049464 A1 | 12/2001 | Ganz |
| 2001/0051669 A1 | 12/2001 | McGhee |
| 2002/0045893 A1 | 4/2002 | Lane et al. |
| 2002/0055666 A1 | 5/2002 | Hunter et al. |
| 2002/0095114 A1 | 7/2002 | Palasis |
| 2002/0177804 A1 | 11/2002 | Saab |
| 2003/0144570 A1 | 7/2003 | Hunter et al. |
| 2004/0039437 A1 | 2/2004 | Sparer et al. |
| 2004/0054366 A1 | 3/2004 | Davison et al. |
| 2004/0087827 A1 | 5/2004 | Lubock |
| 2004/0116767 A1 | 6/2004 | Lebovic et al. |
| 2004/0215048 A1 | 10/2004 | Lubock |
| 2005/0061771 A1 | 3/2005 | Murphy |
| 2005/0080313 A1 | 4/2005 | Stewart et al. |
| 2005/0101823 A1 | 5/2005 | Linares et al. |
| 2005/0124843 A1 | 6/2005 | Singh |
| 2005/0240073 A1 | 10/2005 | Apffelstaedt et al. |
| 2005/0277577 A1 | 12/2005 | Hunter et al. |
| 2006/0020156 A1 | 1/2006 | Shukla |
| 2006/0020256 A1 | 1/2006 | Bell et al. |
| 2006/0100475 A1 | 5/2006 | White et al. |
| 2006/0116546 A1 | 6/2006 | Eng |
| 2006/0136051 A1 | 6/2006 | Furst et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2007/0005003 A1 | 1/2007 | Patterson et al. |
| 2007/0055144 A1 | 3/2007 | Neustadter et al. |
| 2007/0106108 A1 | 5/2007 | Hermann et al. |
| 2007/0270627 A1 | 11/2007 | Cutrer et al. |
| 2008/0057298 A1 | 3/2008 | Finley |
| 2008/0086083 A1 | 4/2008 | Towler |
| 2008/0091055 A1 | 4/2008 | Nguyen et al. |
| 2008/0221384 A1 | 9/2008 | Chi Sing et al. |
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228150 A1 | 9/2008 | Jones et al. |
| 2008/0287801 A1 | 11/2008 | Magnin et al. |
| 2009/0171157 A1 | 7/2009 | Diederich et al. |
| 2009/0188098 A1 | 7/2009 | Acosta et al. |

(56) References Cited

U.S. PATENT DOCUMENTS

FOREIGN PATENT DOCUMENTS

| EP | 0693293 | B1 | 1/1996 |
|---|---|---|---|
| EP | 0719571 | A2 | 7/1996 |
| EP | 0853957 | B1 | 7/1998 |
| EP | 0867200 | A2 | 9/1998 |
| EP | 1051990 | A1 | 11/2000 |
| EP | 1070514 | A1 | 1/2001 |
| EP | 1402922 | A1 | 3/2004 |
| EP | 1541188 | A1 | 6/2005 |
| EP | 1618924 | A1 | 1/2006 |
| JP | 10137250 | A | 5/1998 |
| JP | 2001120561 | A | 5/2001 |
| RU | 2177350 | C2 | 12/2001 |
| WO | 9520241 | A1 | 7/1995 |
| WO | 9712540 | A1 | 4/1997 |
| WO | 9745053 | A2 | 12/1997 |
| WO | 9815315 | A1 | 4/1998 |
| WO | 9934869 | A1 | 7/1999 |
| WO | 0114011 | A1 | 3/2001 |
| WO | 0143826 | A1 | 6/2001 |
| WO | 0158346 | A1 | 8/2001 |
| WO | 0209599 | A2 | 2/2002 |
| WO | 02069862 | A1 | 9/2002 |
| WO | 2004043531 | A2 | 5/2004 |
| WO | 2005037363 | A2 | 4/2005 |
| WO | 2005039655 | A1 | 5/2005 |
| WO | 2005039665 | A1 | 5/2005 |
| WO | 2005067442 | A2 | 7/2005 |
| WO | 2007027831 | A1 | 3/2007 |
| WO | 2007143560 | A1 | 12/2007 |

OTHER PUBLICATIONS

"Variable shield for radiation-therapy source wire and centering catheter", Research disclosure, Mason Publications, Hampshire, GB, vol. 438, No. 48, Oct. 2000, XP007126916.

Gregory K. Edmundson, et al., "Dosimetric Characteristics of the Mammosite RTS, a New Breast Brachytherapy Applicator", Int. J. Radiation Oncology Biol. Phys, vol. 52, No. 4, pp. 1132-1139, 2002.

Melvin A. Astrahan, PhD et al., "Optimization of Mammosite therapy", Int. J. Radiation Oncology Biol. Phys, vol. 58, No. 1, pp. 220-232, 2004.

Philip H. Gutin, et al., "A coaxial catheter system for afterloading radioactive sources for the interstitial irradiation of brain tumors", J. Neurosur, vol. 56, pp. 734-735, 1982.

R.D. Ashpole et al., "A New Technique of Brachytherapy for Malignant Gliomas with Caesium-137; A New Method Utilizing a Remote Afterloading system", Clinical Oncology, (1990).

Abstracts of the 11th International Conference on Brain tumor Research and Therapy Oct. 31-Nov. 3, 1995, Silverado Country Club and Resort, Napa, California, Journal of Neuro-Oncology 28:72, 1996.

Johannesen, T.B. et al, "Intracavity Fractioned Balloon Brachytherapy in Glioblastoma", Acta Neurochir (Wien) (1999) 141: 127-133.

Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.

Stubbs, J. B., et al., "Preclinical Evaluation of a Novel Device for Delivering Brachytherapy to the Margins of Resected Brain Tumor Cavities", J. Neurosurg 96, Feb. 2002, pp. 335-343, vol. 96.

Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.

*SenoRX, Inc.* v. *Hologic, Inc.*; District Court for the District of Delaware, Case No. 1:12-cv-00173-LPS-CJB, Complaint filed Feb. 10, 2012.

*SenoRX, Inc.* v. *Hologic, Inc.*; District Court for the District of Delaware, Case No. 1:12-cv-00173-LPS-CJB, Hologic, Inc.'s Answer to Complaint and Counterclaim filed on May 23, 2012.

*SenoRX, Inc.* v. *Hologic, Inc.*; District Court for the District of Delaware, Case No. 1:12-cv-00173-LPS-CJB, SenoRX's Answer to Counterclaim filed on Jun. 18, 2012.

*SenoRX, Inc.* v. *Hologic, Inc.*; District Court for the District of Delaware, Case No. 1:12-cv-00173-LPS-CJB, Joint Claim Construction Chart, filed Nov. 16, 2012.

*Hologic, Inc., Cytyc Corp., and Hologic L.P.* v. *Senorx, Inc.*; Northern District of California, San Jose Division, Case No. 08-CV-0133 RMW, Defendant Senorx, Inc.'s Notice of Motion and Motion for Summary Udgment of Invalidity ('142 Patent, Claims 1 & 8) and Non-Infringement ('813 Patent, Claims 11 & 12; '204 Patent, Claims 4 & 17), filed May 20, 2009, pp. 7-22, discussing Ashpole, et al., A New Technique of Brachytherapy for Malignant Gliomas with Caesium-137: A New Method for Utilizing a.

Cuttino, L. W., et al., "CT-Guided Multi-Catheter Insertion Technique for Partial Breast Brachytherapy: Reliable Target Coverage and Dose Homogeneity", Brachytherapy 4, 2005, pp. 10-17, Elsevier.

Glasgow, G. P., et al. "Remote Afterloading Technology", AAPM Report No. 41, 1993, pp. i-vi and 1-107, American Institute of Physics, Inc.

Hoshino, T., "Brain Tumor Research Center", Abstracts of the 11th Conference on Brain Tumor Research and Therapy, Journal of Neuro-Oncology 28, 1996, pp. 31-113.

Tanderup, et al, "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.

Devic, et al., "Advantages of Inflatable Multichannel Endorectal Applicator in the Neo-Adjuvant Treatment of Patients with Locally Advanced Rectal Cancer With HDR Brachytherapy", Journal of Applied Clinical Medical Physics, Spring 2005, pp. 44-49, vol. 6, No. 2.

Symon, et al. "Individual Fraction Optimization vs. First Fraction Optimization for Multichannel Applicator Vaginal Cuff High-Dose-Rate Brachytherapy", pp. 211-215, Brachytherapy 5 (2006), Elsevier.

Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.

Walton, R. J., "Therapeutic Uses of Radioactive Isotopes in the Royal Cancer Hospital", The British Journal of Radiology, 1950, pp. 559-599, William Heinemann, Publisher.

Low-Beer, B. V. A., "Radioisotope Therapy", "The Clinical Use of Radioactive Isotopes" 1950, pp. 284-349, Charles C. Thomas, Publisher, Springfield, Illinois, U.S.A., See pp. 343-349.

Low-Beer, B. V. A., "The Therapeutic Use of Radioactive Isotopes", "Practical Therapeutics", Dec. 1954, pp. 69-87, vol. X, No. 6.

Muller, J. H., "Radiotherapy of Bladder Cancer by Means of Rubber Balloons Filled in Situ With solutions of a Radioactive Isotope (Co60)", Cancer, A Journal of the American Cancer Society, Jul.-Aug. 1955, pp. 1035-1043, vol. 8, No. 4, J. B. Lippincott Company, Philidelphia.

Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.

(56) References Cited

OTHER PUBLICATIONS

Hewitt, C. B., et al., "Update on Intracavitary Radiation in the Treatment of Bladder Tumors", The Journal of Urology; Official Journal of the American Urological Association, Inc., 1981, pp. 323-325, vol. 126 September, The Williams & Wilkins Co.

Hieshima, G. B., et al. "A Detachable Balloon for Therapeutic Transcatheter Occlusions 1", Technical Notes, Jan. 1981, pp. 227-228, vol. 138.

Russel, A. H., et al, "Intracavitary Irradiation for Carcinoma of the Urinary Bladder: Rationale, Technique, and Preliminary Results", Int. J. Radiation Oncology. Phys,. 1984, pp. 215-219, vol. 10, Pergamon Press Ltd.

Yin, W., "Brachtherapy of Carcinoma of the Esophagus in China, 1970-1974 and 1982-1984", Brachytherapy HDR and LDR, May 4-6, 1989, pp. 52-56.

Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press plc.

Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.

Fowler, J. F., "Brief Summary of Radiobiological Principles in Fractionated Radiotherapy", Seminars in Radiation Oncology, Jan. 1992, pp. 16-21, vol. 2, No. 1, W. B. Saunders Company.

Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.

Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.

Micheletti, E., et al., "High-Dose-Rate Brachytherapy for Poor-Prognosis, High-Grade Glioma: (Phase II) Preliminary Results", Tumori, 1996, pp. 339-344.

Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. GO974722, Academic Press.

Nag, S., et al., "Remote Controlled High Dose Rate Brachytherapy", Critical Reviews in Oncology/Hematology 22, 1996, pp. 127-150, Elsevier Science Ireland Ltd.

Sylvester, J., et al., "Interstitial Implantation Techniques in Prostate Cancer" Journal of Surgical Oncology 1997; 66: 65-75, Wiley-Liss, Inc.

Tan, L. T., et al., Radical Radiotherapy for Carcinoma of the Uterine Cervix Using External Beam Radiotherapy and a Single Line Source Brachytherapy Technique: The Clatterbridge Technique, The British Journal of Radiology, 70, date Dec. 1997, pp. 1252-1258.

Kuettel, M. R., et al., "Treatment of Female Urethral Carcinoma in Medically Inoperable Patients Using External Beam Irradiation and High Dose Rate Intracavitary Brachytherapy" The Journal of Urology, May 1997, pp. 1669-1671, vol. 157, The American Urological Association, Inc.

Slevin, N. J., et al., "Intracavitary Radiotherapy Boosting for Nasopharynx Cancer" The British Journal of Radiology, 70, Apr. 1997, pp. 412-414.

Sneed, P, K., et al., Interstitial Brachytherapy Procedures for Brain Tumors, Seminars in Surgical Oncology 1997; 13: 157-166, Wiley-Liss, Inc.

Dempsey, J. F., et al., "Dosimetric Properties of a Novel Brachytherapy Balloon Applicator for the Treatment of Malignant Brain-Tumor Resection-Cavity Margins" Int. J. Radiation Oncology Biol. Phys., May 1998, pp. 421-429, vol. 42, No. 2, Elsevier.

Kolotas, C., et al., "CT Guided Interstitial High Dose Rate Brachytherapy for Recurrent Malignant Gliomas", The British Journal of Radiology, 72, (1999), pp. 805-808.

Demanes, D, J., et al., "The Use and Advantages of a Multichannel Vaginal Cylinder in High-Dose-Rate Brachytherapy", Int. J. Radiation Oncology Biol. Phys., (1999), pp. 211-219, vol. 44, No. 1, Elsevier Science Inc.

Debicki, M. P., et al., "Localized Current Field Hyperthermia in Carcinoma of the Cervix: 3-D Computer Simulation of SAR Distribution", International Journal of Hyperthermia, 1999, pp. 427-440, vol. 15, No. 5.

Garipagaoglu, M, et al., "Geometric and Dosimetric Variations of ICRU Bladder and Rectum Reference Points in Vaginal Cuff Brachytherapy Using Ovoids", Int. J. Radiation Oncology Biol. Phys.. 2004, pp. 1607-1615, Elsevier Inc.

Bowsher, W. G., et al., "Update on Urology-Prostate Cancer, 4-Treatment of Local Disease", European Journal of Surgical Oncology, 1995 pp. 679-682, vol. 21, No. 6.

Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.

Harada, T, et al., "Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.

Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, 50/3/MAR.

Hine, G. J., et al., "Isodose Measurements of Linear Radium Sources in Air and Water by Means of an Automatic Isodose Recorder", The American Journal of Roentgenology and Radium Therapy, 1950, pp. 989-998, vol. 64, No. 6, The Societies.

Walton, R. J., et al., Radioactive Solution (24Na and 82 Br) in the Treatment of Carcinoma of the Bladder:, British Medical Bulletin, 1952, pp. 158-165, Medical Dept., The British Council.

Marshall V. F., et al., "Current Clinical Problems Regarding Bladder Tumors", Symposium on Bladder Tumors, 1956, pp. 543-550, 9/3/May-Jun, J. B. Lippincott Co, Etc.

Hewitt, C. B., et al., "Intracavitary Radiation in the Treatment of Bladder Tumors", The Journal of Urology, vol. 107, Apr. 1972, pp. 603-606, The Williams & Wilkins Co.

Rotman, M., et al., "The Intracavitary Applicator in Relation to Complications of Pelvic Radiation—The Ernst System", Int. J. Radiation Oncology Biol. Phys., 1978, pp. 951-956, vol. 4, Pergamon Press Inc.

Nag, S., et al., "The Future of High Dose Rate Brachytherapy", High Dose Rate Brachytherapy: A Textbook, 1994, pp. 447-453, Futura Publishing Company, Inc. , Armonk, New York 10504.

Wang, C. C., "Carcinoma of the Nasopharynx", Radiation Therapy of Head and Neck Neoplasms, 1997, pp. 257-280, Chapter 10, Wiley-Liss, Inc.

Gaspar, L. E., et al., "Esophageal Brachytherapy", Principles and Practice of Brachytherapy, 1997, pp. 305-321, Futrua Publishing Company, Inc., Armouk, New York.

Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.

Akagi, Y, et al., "Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.

(56) References Cited

OTHER PUBLICATIONS

XP007904995:retrieved from the internet: URL: http://www2.dupont.com/Teflon_Industrial/en_US/assets/downloads/h88800.pdf; retrieved on Jun. 19, 2008, by Authorized Officer in International Application PCT/US2008/003364.

Lewis, J, et al., "Intracranial Brachytherapy Using a High Dose Rate Microselectron", Northern Centre for Cancer Treatment, Dept. of Neurosciences, Regional Medical Physics Department, Newcastle General Hospital, Newcastle Upon Tyne, UK, Radiation and Oncology, vol. 39, Supplement 1, May 1996, pp. 45-45(1).

International Search Report for PCT/US2008/003364 mailed Aug. 27, 2008.

Written Opinion of the International Searching Authority for PCT/US2008/003364 dated Sep. 15, 2009.

International Preliminary Report on Patentability for PCT/US2008/003364 issued Aug. 3, 2010.

International Search Report for PCT/US2008/003217 mailed Aug. 12, 2008.

Written Opinion of the International Searching Authority for PCT/US2008/003217 dated Sep. 12, 2009.

International Preliminary Report on Patentability for PCT/US2008/003217 dated Mar. 21, 2011.

International Search Report for PCT/US03/33775 mailed Jun. 21, 2004.

International Preliminary Report on Patentability for PCT/US03/33775 dated Oct. 10, 2007.

International Search Report for PCT/US2006/044067 mailed Dec. 18, 2007.

Written Opinion of the International Searching Authority for PCT/US2006/044067 dated Jan. 11, 2009.

International Preliminary Report on Patentability for PCT/US2006/044067 dated Oct. 2, 2009.

International Search Report for PCT/US2006/043891 mailed Sep. 25, 2007.

Written Opinion of the International Searching Authority for PCT/US2006/043891 dated May 18, 2008.

International Preliminary Report on Patentability for PCT/US2006/043891 dated Jan. 12, 2009.

International Search Report for PCT/US2009/000402 mailed Apr. 15, 2009.

Office Action dated Feb. 1, 2013 in U.S. Appl. No. 13/571,495.

* cited by examiner

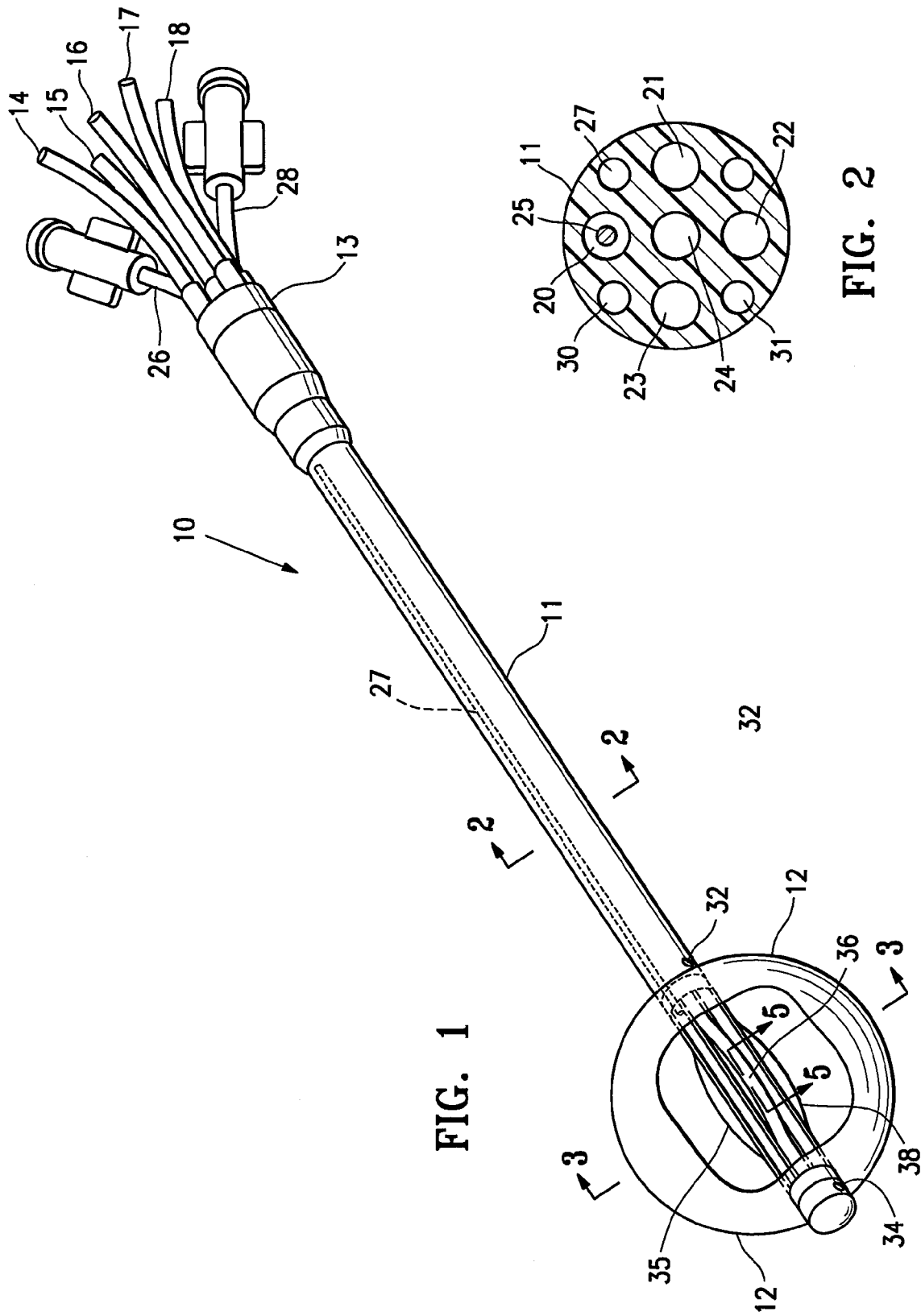

RADIATION CATHETER WITH MULTILAYERED BALLOON

CROSS REFERENCE TO RELATED APPLICATIONS

This application is a continuation of U.S. patent application Ser. No. 11/716,758 filed Mar. 12, 2007, which is hereby incorporated by reference in its entirety.

FIELD OF THE INVENTION

This invention relates generally to the fields of medical treatment devices and methods of use. In particular, the invention relates to devices and methods for irradiating tissue surrounding a body cavity, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver radiation to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The delivery lumen of the device may receive a solid or a liquid radiation source. Radiation treatment is applied to tissue adjacent the balloon of the device by placing radioactive material such as radioactive "seeds" in a delivery lumen. Such treatments may be repeated if desired.

For example, a "MammoSite® Radiation Therapy System" (MammoSite® RTS, which is available from Proxima Therapeutics, Inc., Alpharetta, Ga. 30005 USA) includes a balloon catheter with a radiation source or configured to receive a radiation source that can be placed within a tumor resection cavity in a breast after a lumpectomy. It can deliver a prescribed dose of radiation from inside the tumor resection cavity to the tissue surrounding the original tumor. The radiation source is typically a solid radiation source; however, a liquid radiation source may also be used with a balloon catheter placed within a body cavity (e.g., Lotrex®, a liquid radiation source available from Proxima Therapeutics, Inc.). A radiation source such as a miniature or microminiature x-ray tube catheter may also be used (e.g. U.S. Pat. No. 6,319,188). The x-ray tube catheters are small, flexible and are believed to be maneuverable enough to reach the desired treatment location within a patient's body. The radiation source may be removed following each treatment session, or may remain in place as long as the balloon remains within the body cavity. Inflatable radiation treatment delivery devices and systems, such as the MammoSite® RTS and similar devices and systems (e.g., GliaSite® RTS) which are available from (Proxima Therapeutics, Inc.)), are useful to treat cancer in tissue adjacent a body cavity.

Tissue cavities resulting from biopsy or other surgical procedures such as lumpectomy typically are not always uniform or regular in their sizes and shapes, so that radiation treatment often result in differences in dosages applied to different regions of surrounding tissue, including "hot spots" and regions of relatively low dosage. However, by conforming the tissue lining the cavity about an inflated member, such as a balloon, a more uniform or controlled radiation can be applied to the tissue.

However, making a robust, inflatable balloon which has a predictable inflated size and shape can be problematic, particularly with a balloon size suitable for breast biopsy/lumpectomy cavities which range from about 0.5 to about 4 inches in maximum diameter, and are typically about 2 inches.

SUMMARY OF THE INVENTION

This invention is generally directed to irradiating tissue surrounding a patient's body cavity, and particularly to devices and methods for such treatments. The invention is particularly suitable for treating tissue adjacent a patient's body cavity formed by removal of tissue for a biopsy or lumpectomy.

More specifically, a device embodying features of the invention includes an elongated shaft with a treatment location at a distal portion of the shaft which is configured to receive or which includes a radiation source and an inflatable cavity filling member or balloon surrounding the treatment location on the distal shaft portion having two or more layers of compliant or semi-compliant polymeric materials. In this embodiment, the polymeric material of one or more of the multiple layers of the inflatable balloon in a formed but un-inflated condition has limited expansion to a turgid inflated condition with the balloon material at or near the material's elastic limit. The balloon's expansion from an initial formed condition to an inflated turgid condition should be less than 200%, preferably less than 175% and should be more than 25%. Typically, the expansion should be about 50% to about 150%. The residual stress in the formed polymeric material of the one or more layers of the balloon should be the result of an expansion of the external surface area of a balloon to the surface area of the balloon in the initial formed condition. This expansion can be represented by the ratio of the external surface area of the initially formed condition of the balloon to the to-be-expanded external surface area of the balloon preform represented as a percentage of the to-be-expanded surface area of the balloon preform. This ratio should be not more than 1000%, preferably less than 800% from a pre-form such as a tube. Preferably, the pre-form is an extruded product. The process of expansion may involve heating the preform and the level of residual stress in the balloon material at the initial formed condition may be dependent on the temperature of the preform during the expansion and the time dependant profile of the heating and cooling cycle of the material during expansion.

The multiple layers of the inflatable cavity filling member should be formed of a thermoplastic elastomeric polymer such as polyester polyurethane, e.g. Pellethane™ which is available from Dow Chemical. Preferably the polymeric material has a Shore Durometer of 90A. Other suitable polymeric materials may be employed. The polymeric material of the balloon layers may be a blend of polymers or a copolymer.

Balloons of this type are often filled with a radiopaque fluid for visualization for positional and symmetry verification and CT for positional verification and radiation dose planning. The balloons themselves may be radiopaque by compounding radiopaque agents into the balloon material, coating the inside and/or outside surfaces of a balloon layer with radiopaque material or providing a radiopaque material between balloon layers. Radiopaque agents or materials may be one or more metals of the group consisting of tantalum, tungsten, rhenium, titanium and alloys thereof or compounds containing oxides of titanium or barium salts such as those which are often used as pigments.

A radiation catheter device embodying features of the invention preferably has an inflatable cavity filling member or balloon at the treatment location which is configured to at least in part fill the body cavity to be treated. The device also may include an inner lumen configured to be in fluid communication with a proximal vacuum source and one or more vacuum ports preferably proximal and/or distal to the cavity filling member such as described in U.S. Pat. No. 6,923,754 and co-pending application Ser. No. 10/849,410, filed on May 19, 2004, both of which are assigned to the present assignee. Application of a vacuum within the inner lumen aspirates fluid in the cavity through the one or more vacuum ports and the application of a vacuum within the body cavity pulls tissue defining the cavity onto the exterior of the inflated cavity filling member deployed within the cavity so as to conform the tissue lining to the shape of the cavity filling member.

Methods previously described in co-pending application Ser. No. 11/357,274, filed on Feb. 17, 2006 and Ser. No. 11/593,789, filed on Nov. 6, 2006 for using radiation catheters are suitable for a radiation catheter embodying features of the invention body cavity. The present invention however, provides enhanced control over the expansion of the balloon and a more predictable ultimate balloon size and shape. These and other advantages of the present invention are described in more detail in the following detailed description and the accompanying exemplary drawings.

BRIEF DESCRIPTION OF THE DRAWINGS

FIG. 1 is a perspective view of a catheter device embodying features of the invention including a multilayered balloon.

FIG. 2 is a transverse cross section of the catheter shaft taken along the lines 2-2 shown in FIG. 1.

DETAILED DESCRIPTION OF THE INVENTION

Figure 4:
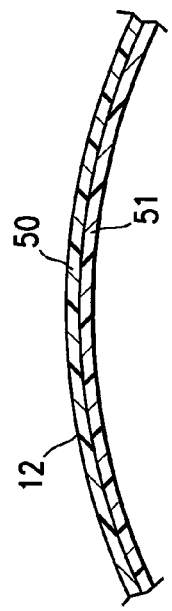
FIG. 4 is an enlarged sectional view of the balloon wall shown in the circle 4-4 in FIG. 3 to illustrate the multiple layers thereof.
Figure 5:
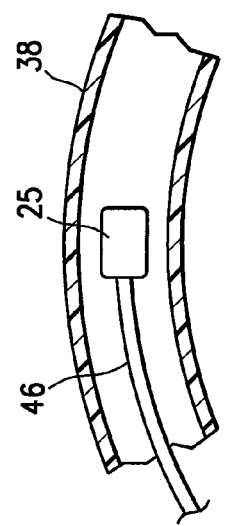
FIG. 5 is an enlarged longitudinal cross-section of a radiation tube taken along the lines 5-5 shown in FIG. 1 to illustrate the deployment of a radiation source within the treatment location.

The present invention provides devices and methods for treatment of a patient's body cavity. For example, devices and methods having features of the invention are used to deliver radiation or other treatment into a biopsy site or into a cavity left after removal of cancerous tissue from the patient's body.

FIGS. 1-5 illustrate a catheter device 10 which has an elongated shaft 11, a cavity filling member or balloon 12 on the distal portion of the shaft which for the most part defines the treatment location, and an adapter 13 on the proximal end of shaft 11. A plurality of tubes 14-18 extend into the adapter 13 and are in fluid communication with lumens 20-24 respectively within the shaft 11 which are configured to receive one or more radiation sources 25. The device 10 also has an inflation tube 26 which is in fluid communication with inflation lumen 27 that extends to and is in fluid communication with the interior of the balloon 12 to facilitate delivery of inflation fluid thereto. The inflation fluid may be radiopaque to facilitate imaging of the balloon and shaft within the patient. The lumen 27 is shown filled with radiopaque fluid in FIG. 1. The adapter 13 also has a vacuum tube 28 that is in fluid communication with lumens 30 and 31. Lumen 30 is in fluid communication with proximal vacuum port 32 and lumen 31 is in fluid communication with tubular member 33 which extends across the interior of balloon 12 and which in turn is in fluid communication with distal vacuum port 34. Radiation delivery tubes 35-39 extend through the interior of balloon 12 and are in fluid communication with lumens 20-24 within shaft 11. The radiation delivery tubes 35, 36, 38 and 39 extend radially away from a center line axis 40 within the interior of balloon 12 in order to position a radiation source 25 closer to a first tissue portion surrounding a body cavity than a second tissue portion. While tubes 35, 36, 38 and 39 are shown as being slightly radially extended within the interior of balloon 12, less than all of them may radially extend within the balloon 12 depending upon the need for a particular treatment. Moreover, tubes 35, 36, 38 and 39 may be in a contracted state within recesses of support member 41, and one or more of the tubes may be radially extended out of the recesses after the balloon 12 is deployed within a cavity at the target body site.

The support element 41, which extends between the proximal and distal ends of the balloon 12, has four compartments 42-4 which are designed to receive tubular radiation delivery members 35, 36, 38 and 39 respectively. The radiation delivery tubes will not usually be radially extended to the extent that they contact the interior surface of the balloon 12 in an inflated condition.

Figure 3:
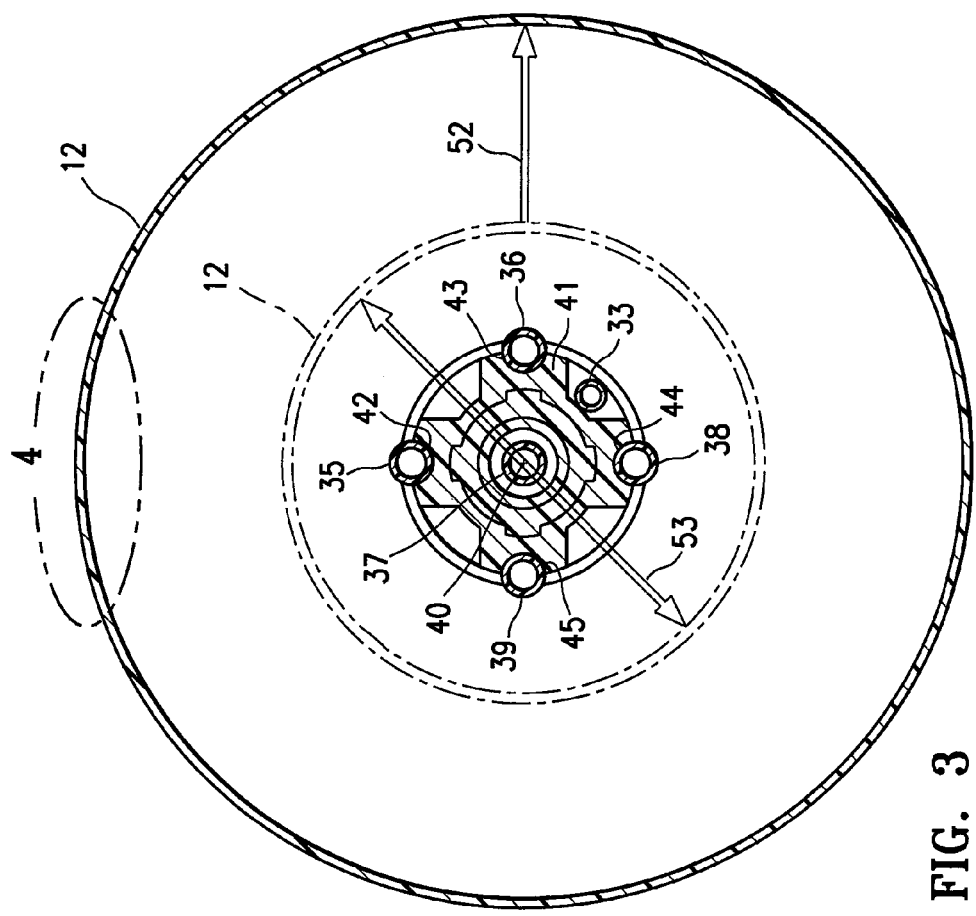
FIG. 3 is an enlarged transverse cross sectional view of the multilayered balloon wall shown in FIG. 2.

The balloon 12 is provided with two separate layers 50 and 51 as shown in FIG. 4. The expansion of the balloon 12 is illustrated in FIG. 3 with the balloon in an as formed, non-turgid condition shown in phantom. The arrow 52 illustrates the expansion of the balloon from the formed condition to the turgid condition. The expansion is less than 200% of the initial as formed condition (diameter shown as arrow 53), preferably less than 175% and is typically about 75 to about 125% of the initial balloon volume. While the inflated, turgid balloon 12 is shown as being spherical in shape, other shapes may be suitable, such as an ovoid shape. Depending upon the material and the conditions at the body site, the wall of the turgid balloon may relax somewhat after reaching the turgid condition. The thicknesses of the balloon wall layers can vary depending upon the material characteristics and the number of layers. Typically, the thickness of individual balloon wall layers range from about 0.0003 to about 0.006 inch, preferably about 0.001 to about 0.002 inch. The total thickness of the balloon wall is about 0.0006 to about 0.012 inch, preferably about 0.002 to about 0.004 inch.

The radiation delivery tubes 14-18, which extend into the adapter 13, may extend through the lumens 20-24 in shaft 11 and may form tubes 35-39 which are received by the support member 40 and extend into the interior of balloon 12.

All of the radiation delivery tubes which extend through the interior of the balloon 12 would not necessarily be used in a particular irradiation procedure, but they would be available for use by the physician if needed, e.g. when the balloon 12 of the radiation catheter 10 is not in a desired position and rotation of the catheter is not appropriate or desirable. The shaft 11 is shown as a solid shaft having a plurality of passageways. However, the shaft 11 may be made more flexible by utilizing a plurality of elongated tubes 14-18 which are bundled together to form the shaft. Multiple bands may encircle the tubular members along their length to hold the tubular members together.

The radiation source 25 for the brachytherapy device 10 is shown as a radiation seed on the distal end of rod 46. However, the radiation source 25 may be a solid or liquid radiation source. Suitable liquid radiation sources include, for example, a liquid containing a radioactive iodine isotope (e.g., $I^{125}$ or $I^{131}$), a slurry of a solid isotope, for example, $^{198}Au$ or $^{169}Yb$, or a gel containing a radioactive isotope. Liquid radiation sources are commercially available (e.g., Lotrex®, Proxima Therapeutics, Inc., Alpharetta, Ga.). The radiation source 25 preferably includes brachytherapy seeds or other solid radiation sources used in radiation therapy. A catheter with a micro-miniature x-ray source may also be utilized. The radiation source 25 may be either preloaded into the device 10 at the time of manufacture or may be loaded into the device 10 before or after placement into a body cavity or other site of a patient. Solid radionuclides suitable for use with a device 10 embodying features of the present invention are currently generally available as brachytherapy radiation sources (e.g., I-Plant™ a solid radiation source from Med-Tec, Orange City, Iowa.). Radiation may also be delivered by a micro-miniature x-ray device such as described in U.S. Pat. No. 6,319,188. The x-ray tubes are small, flexible and are believed to be maneuverable enough to reach the desired location within a patient's body.

The radiation source 25 of the device 10 can include a radiation source which is solid or liquid or both, e.g. a slurry. Suitable liquid radiation sources include, for example, a liquid containing a radioactive iodine isotope (e.g., $I^{125}$ or $I^{131}$), a slurry of a solid isotope, for example, $^{198}AU$ or $^{169}Yb$, or a gel containing a radioactive isotope. Liquid radiation sources are commercially available (e.g., Lotrex®, Proxima Therapeutics, Inc., Alpharetta, Ga.). The radiation source 18 preferably is one or more brachytherapy seeds, for example, a radioactive microsphere available from 3M Company of St. Paul, Minn. Other suitable brachytherapy radiation sources include I-Plant™, (Med-Tec, Orange City, Iowa.). Radiation may also be delivered by a microminiature x-ray tube catheter such as described in U.S. Pat. No. 6,319,188. X-ray tube catheters are small, flexible and are believed to be maneuverable enough to reach the desired location within a patient's body.

The device 10 can be provided, at least in part, with a lubricious coating, such as a hydrophilic material. The lubricious coating preferably is applied to the elongate shaft 11 or to the balloon 12 or both, to reduce sticking and friction during insertion and withdrawal of the device 10. Hydrophilic coatings such as those provided by AST, Surmodics, TUA Systems, Hydromer, or STS Biopolymers are suitable. The surfaces of the device 10 may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating may also be an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating may be provided on the elongated shaft of the delivery device 10 at the point where the device 10 enters the patient's skin.

The balloon 11 may also be provided with radiopaque material to facilitate detection during CT, X-ray or fluoroscopic imaging. Such imaging allows the physician or other staff to detect the size and shape of the balloon and whether the balloon is properly located at the desired location. Preferably, the exterior surface of an inner layer of the balloon is coated at least in part with radiopaque material. One suitable method for coating the surface of the layer is to mix a polymer, preferably essentially the same polymer of the layer, with a solvent such as tetrahydrofuran and a radiopaque agent such as a powdered metallic material, e.g. titanium, gold, platinum and the like, or other suitable radiopaque materials. The mixture is applied to the exterior surface of an inner balloon layer and the solvent is allowed to evaporate, leaving the radiopaque material and the polymer bonded to the balloon layer. The multiple layers of the balloon are then secured to the catheter shaft.

The device 10 may be used to treat a body cavity of a patient, e.g. a biopsy or lumpectomy site within a patient's breast, in the manner described in the previously referred to co-pending applications. Usually the adapter 13 on the proximal end of the catheter device extends out of the patient during the procedure when the balloon is inflated. The catheter shaft 11 is preferably flexible enough along a length thereof, so that once the balloon is inflated to its turgid condition, the catheter shaft can be folded or coiled and placed under the patient's skin before the exterior opening of the treatment passageway to the treatment site is closed. At the end of the treatment time, e.g. 5-10 days, the exterior opening can be reopened and the catheter removed from the patient. See for example the discussion thereof in previously discussed co-pending application Ser. No. 11/357,274.

Radiation balloon catheters for breast implantation generally are about 6 to about 12 inches (15.2-30.5 cm) in length, typically about 10.6 inch (27 cm). The shaft diameter is about 0.1 to about 0.5 inch (2.5-12.7 mm), preferably about 0.2 to about 0.4 inch (5.1-10.2 mm), typically 0.32 inch (8 mm). The individual radiation lumens are about 0.02 to about 0.15 inch (0.5-3.8 mm), preferably about 0.04 to about 0.1 inch (1-1.5 mm). The balloons are designed for inflated configurations about 0.5 to about 4 inches (1.3-10.2 cm), typically about 1 to about 3 inches (2.5-7.5 cm) in transverse dimensions, e.g. diameters.

While particular forms of the invention have been illustrated and described herein, it will be apparent that various modifications and improvements can be made to the invention. To the extent not previously described, the various elements of the catheter device may be made from conventional materials used in similar devices. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "manufacture", "portion", "section", "steps" and words of similar import when used herein shall not be construed as invoking the provisions of 35 U.S.C. §112(6) unless the following claims expressly use the terms "means for" or "step for" followed by a particular function without reference to a specific structure or action. All patents and all patent applications referred to above are hereby incorporated by reference in their entirety.

What is claimed is:

1. A catheter device for irradiating tissue surrounding a body site within a body of a patient, comprising:
   an elongated shaft which has a distal portion configured to be deployed within the body site;
   a radiation source;
   a treatment location at the distal portion having one or more radiation guides configured to receive the radiation source to irradiate tissue at least in part surrounding the body site; and
   an inflatable multilayered balloon located to surround the treatment location with a wall thereof having at least two layers including a first layer separate from, inside, and in contact with a second layer around an entire periphery of the first layer when in an as formed configuration and an inflated configuration, and each of the first layer and the second layer being secured to the distal portion of the elongated shaft and configured to surround the treatment location in the as formed configuration and the inflated configuration.

2. The catheter device of claim 1, wherein the inflatable multilayered balloon has a predetermined size and shape when the at least two layers thereof are in the turgid condition.

3. The catheter device of claim 1, wherein the inflatable multilayered balloon has an expansion of at least 25% but less than 200% from the as formed configuration when the inflatable multilayered balloon is inflated to a turgid condition.

4. The catheter device of claim 1, wherein the at least two layers of the inflatable multilayered balloon have expansions of about 50% to about 150% when inflated from the as formed configuration to the turgid condition.

5. The catheter device of claim 1, wherein the at least two layers of the inflatable multilayered balloon has an expansion of less than 175% when inflated from the as formed configuration to the turgid condition.

6. The catheter device of claim 1, wherein each of the first layer and the second layer of the inflatable multilayered balloon has an individual thickness of about 0.0003 to about 0.006 inch thick.

7. The catheter device of claim 1, wherein the at least two layers of the inflatable multilayered balloon are about 0.001 inch to about 0.002 inch thick.

8. The catheter device of claim 1, wherein the total combined thickness of the first layer and the second layer of the inflatable multilayered balloon is about 0.002 inch to about 0.004 inch.

9. The catheter device of claim 1, comprising an off-set tubular member configured to receive the radiation source, which is off-set from a central longitudinal axis so that in the treatment location the radiation source is closer to a first portion of tissue at the body site than a second portion of tissue.

10. The catheter device of claim 1, wherein the one or more radiation guides in the distal portion of the elongated shaft comprises a plurality of radiation delivery tubes configured to receive the radiation source.

11. A catheter device for irradiating tissue surrounding a body site within a body of a patient, comprising:
   an elongated shaft which has a distal portion configured to be deployed within the body site and a central longitudinal axis;
   a radiation source
   a treatment location at the distal portion having one or more radiation guides configured to receive the radiation source, with at least one radiation guide off-set from the central longitudinal axis to position the radiation source at a location offset from the central longitudinal axis; and
   an inflatable multilayered balloon located to surround the treatment location, the inflatable multilayered balloon having a wall that has at least two layers including a first layer separate from, inside, and in contact with a second layer around an entire periphery of the first layer when in an as formed configuration and an inflated configuration, and each of the first layer and the second layer being secured to the distal portion of the elongated shaft and configured to surround the treatment location in the as formed configuration and the inflated configuration.

12. The catheter device of claim 11, wherein the inflatable multilayered balloon has a predetermined size and shape when the at least two layers thereof are in the turgid condition.

13. The catheter device of claim 11, wherein the inflatable multilayered balloon has an expansion of at least 25% but less than 200% from the as formed configuration when the inflatable multilayered balloon is inflated to a turgid condition.

14. The catheter device of claim 11, wherein the at least two layers of the inflatable multilayered balloon has an expansion of less than 175% when inflated from the as formed configuration to the turgid condition.

15. The catheter device of claim 11, wherein the at least two layers of the inflatable multilayered balloon have expansions of about 50% to about 150% when inflated from the as formed configuration to the turgid condition.

16. The catheter device of claim 11, wherein each of the first layer and the second layer of the inflatable multilayered balloon has an individual thickness of about 0.0003 inch to about 0.006 inch thick.

17. The catheter device of claim 11, wherein the at least two layers of the inflatable multilayered balloon are about 0.001 inch to about 0.002 inch thick.

18. The catheter device of claim 11, wherein the total combined thickness of the first layer and second layer of the inflatable multilayered balloon is about 0.002 inch to about 0.004 inch.

19. The catheter device of claim 11, wherein the one or more radiation guides in the distal portion of the elongated shaft comprise a plurality of radiation delivery tubes in fluid communication with a respective plurality of tubular members that extend through the elongated shaft, and with each of the plurality of tubular members configured to receive the radiation source and advance the radiation source to a respective radiation delivery tube of the plurality of radiation delivery tubes.

20. The catheter device of claim 11, comprising:
at least one vacuum port, each vacuum port being located on the elongated shaft at a location that is one of proximal and distal to the inflatable multilayered balloon; and
a vacuum lumen longitudinally extending through the elongate shaft and configured to be in fluid communication with the at least one vacuum port.

* * * * *